United States Patent [19]

Desposato et al.

[11] 4,219,641
[45] Aug. 26, 1980

[54] PROCESS FOR PREPARING ERYTHROMYCIN SUCCINATE

[75] Inventors: Francis E. Desposato; Edward J. Hessler, both of Kalamazoo, Mich.

[73] Assignee: The Upjohn Company, Kalamazoo, Mich.

[21] Appl. No.: 48,510

[22] Filed: Jun. 14, 1979

Related U.S. Application Data

[63] Continuation-in-part of Ser. No. 970,342, Dec. 18, 1978, abandoned.

[51] Int. Cl.² .................. C07H 17/08; A61K 31/70
[52] U.S. Cl. .................... 536/9; 536/17 R; 424/180
[58] Field of Search .................. 536/9; 536/17

[56] References Cited

U.S. PATENT DOCUMENTS

| | | | |
|---|---|---|---|
| 2,857,312 | 10/1958 | Stephen | 536/9 |
| 2,967,129 | 1/1961 | Clark | 536/9 |
| 3,853,842 | 12/1974 | Kishi et al. | 536/9 |

*Primary Examiner*—Johnnie R. Brown
*Assistant Examiner*—Blondel Hazel
*Attorney, Agent, or Firm*—Roman Saliwanchik

[57] ABSTRACT

A rapid and efficient process for preparing the useful antibiotic erythromycin ethyl succinate in high yield which comprises reacting erythromycin USP quality free base with ethyl succinyl chloride in a two phase system consisting of an organic solvent which is capable of forming two phases with water or an aqueous base, and an aqueous base.

12 Claims, No Drawings

PROCESS FOR PREPARING ERYTHROMYCIN SUCCINATE

CROSS REFERENCE TO RELATED APPLICATION

This application is a continuation-in-part of our pending application Ser. No. 970,342, filed on Dec. 18, 1978, now abandoned.

BACKGROUND OF THE INVENTION

U.S. Pat. No. 2,967,129 discloses a process in Example 1 for preparing erythromycin ethyl succinate. This process uses erythromycin free base, sodium bicarbonate and ethyl succinyl chloride in acetone. As is readily apparent from the patent disclosure, the reaction is very slow and the yield is rather low, approximately 56%.

BRIEF SUMMARY OF THE INVENTION

Upon reacting erythromycin USP quality free base with ethyl succinyl chloride in a two phase system consisting of an organic solvent which is capable of forming two phases with water or an aqueous base, and an aqueous base there is produced erythromycin ethyl succinate in high yield. For example, when tetrahydrofuran is the organic solvent used, there is produced erythromycin ethyl succinate in a weight yield of about 100% with an activity of about 837 mcg/ml. The process yield on an activity basis is approximately 90%. Thus, the subject process is considerably more efficient than the best prior art process known, as disclosed above, to make erythromycin ethyl succinate.

DETAILED DESCRIPTION OF THE INVENTION

The subject process for preparing erythromycin ethyl succinate uses, advantageously, erythromycin USP quality free base as the starting material. This material is readiy available on the market. The "USP" denotes the quality standards promulgated by the United States Pharmacopeia. The use of erythromycin USP as the starting material insures that the final product, i.e., erythromycin ethyl succinate, will meet the rigid USP standards which include bioavailability.

The organic solvent used in the subject process must be capable of forming two phases with water or aqueous base. Examples of such an organic solvent is tetrahydrofuran (preferred), isopropanol, acetone, methyl ethyl ketone, ethyl acetate, and the like. Tetrahydrofuran is the preferred solvent because, when it is used, the desired product crystallizes in large crystals. These large crystals facilitate the subsequent filtration step. Use of ethyl acetate as the organic solvent must be accompanied by the addition of hexane to crystallize the desired product.

The erythromycin USP is dissolved in a sufficient quantity of organic solvent, as described above, to maintain a solution at about 20° C. to about 40° C., preferably at about 35° C. To this solution is added a sufficient amount of a base, for example, a potassium carbonate solution, and water to maintain the pH of the aqueous phase between about 7 and about 8.5. Further, the potassium carbonate must be about 2.2% or greater of the aqueous phase in order to obtain the desired two phase reaction system. Other bases can be used so long as the pH of the base solution is about 9 to about 10. Examples of other bases are sodium carbonate, sodium hydroxide, potassium hydroxide, and the like.

The above stirred mixture of erythromycin USP in organic solvent and potassium carbonate solution is cooled to about 10° C. to about 35° C., preferably to about 18° C. to about 20° C. Ethyl succinyl chloride is then added over a period of about one hour. The reaction can be followed by thin layer chromatography (tlc) using a solvent system consisting of 10% methanol in methylene chloride. The quantity of ethyl succinyl chloride should be sufficient to complete the reaction as evidenced by tlc. A large excess of ethyl succinyl chloride will cause over acylation.

The addition of ethyl succinyl chloride can be over a period of about 45 minutes to about 120 minutes. An addition rate of about one hour is preferable since a faster addition rate may cause a temperature control problem, whereas a slower addition rate extends the time available for product hydrolysis.

The pH of the aqueous phase will be between about 7.0 and about 8.5 upon completion of the above-described reaction.

After increasing the temperature of the reaction mixture to about 32° C. to about 40° C., preferably about 35° C., a heavy metals scavenger is added, for example, sodium citrate (preferred), ethylene diamine tetraacetic acid tetra sodium salt, or nitrilo triacetic acid tri sodium salt. The amount of heavy metals scavenger used is not critical and can range from 0 to 100% saturation of the aqueous phase. This salt remains in the aqueous phase and is separated later in the process.

The above mixture is stirred for about 15 minutes to about 60 minutes, preferably for about 30 minutes, to allow for complete equilibration. Undue extension of this time will result in some product loss.

The reaction mixture is then subject to clarification and crystallization procedures to yield erythromycin ethyl succinate. These procedures can be as follows with obvious variations well within the skill of those in the antibiotic art.

After the above time period, the stirring is stopped, the lower phase settles and is separated from the reaction mixture. A sufficient amount of diatomaceous earth, for example, Celite, is added to the remaining organic solution to remove any insoluble foreign particles. The solution is filtered and then cooled to about 18° C. to about 20° C. Water is then added to reduce the solubility of the erythromycin ethyl succinate and to allow for crystallization in the temperature range of about 18° C. to about 20° C. The amount of water to be added can be gauged by observing the clarity of the solution, i.e. when the solution becomes hazy, then a sufficient amount of water has been added.

After the solution becomes hazy, it is seeded with erythromycin ethyl succinate crystals. Subsequent procedures of cooling, filtration, washing, and drying, yields high quality erythromycin ethyl succinate crystals which meet the demanding requirements of the USP, and bioavailability. The aqueous tetrahydrofuran reaction system, disclosed above, results in high yields (>90% activity to activity) improved crystallization of the final product, and a much higher crystal filtration rate.

The following examples are illustrative of the process and products of the invention, but are not to be construed as limiting. All percentages are by weight and all solvent mixture proportions are by volume unless otherwise noted.

EXAMPLE 1

Preparation Of Erythromycin Ethyl Succinate From Erythromycin

Erythromycin (dihydrate) USP 60 gms are dissolved in 208 mls of tetrahydrofuran in a stirred reactor. 93 gms of 47% $K_2CO_3$ solution and 178 mls of water are added. The stirred mixture is cooled to 18° C. and 36.7 gms of ethyl succinyl chloride are added over about a 1 hour period to complete the reaction which is so indicated by tlc. The pH of the aqueous phase is measured and should be between 7.0 and 8.5 Sodium citrate (3.0 g) is added and the temperature of the stirred mixture is increased to 35° C. After ½ hour stirring the lower phase is settled and separated. Celite is added to the remaining organic solution and mixed followed by filtration. The clarified solution is cooled to 18° C. to 20° C., water added until the solution becomes hazy, about 50 mls, followed by seeding with crystals or erythromycin ethyl succinate. After a good slurry has developed the remainder of the water, about 450 mls, is added slowly. The slurry is stirred at about 15° C. for 1 hour and then filtered and washed. The filter cake is dried at 50° C. to 60° C. under vacuum. A 95–105% weight yield is normal.

We claim:

1. A process for preparing erythromycin ethyl succinate which comprises reacting erythromycin USP quality free base with ethyl succinyl chloride in a two phase system consisting of an organic solvent which is capable of forming two phases with water or an aqueous base, and an aqueous base.

2. A process, according to claim 1, wherein said organic solvent is tetrahydrofuran.

3. A process, according to claim 1, wherein said aqueous base is a potassium carbonate solution.

4. A process for preparing erythromycin ethyl succinate which comprises:
   (a) dissolving erythromycin USP quality free base in sufficient quantity in an organic solvent which is capable of forming two phases with water or an aqueous base, and an aqueous base to maintain a solution at about 20° C. to about 40° C.;
   (b) adding a sufficient amount of a base solution and water to maintain the pH of the aqueous phase between about 7 and about 8.5 to obtain a mixture of erythromycin USP quality free base in tetrahydrofuran and base solution;
   (c) cooling said mixture to about 10° C. to about 35° C.;
   (d) adding ethyl succinyl chloride to said cooled mixture;
   (e) increasing the temperature of the reaction mixture to about 32° C. to about 40° C. and adding a heavy metals scavenger;
   (f) stirring said mixture to allow for complete equilibration;
   (g) separating the resulting lower phase from the reaction mixture;
   (h) clarifying the remaining organic solution; and,
   (i) crystallizing erythromycin ethyl succinate.

5. A process, according to claim 4, wherein a sufficient quantity of erythromycin USP quality free base is dissolved in tetrahydrofuran to maintain a solution at about 35° C.

6. A process, according to claim 4, wherein said base solution is a potassium carbonate solution.

7. A process, according to claim 4, wherein said mixture of erythromycin USP quality free base in tetrahydrofuran and base solution is cooled to about 18° C.

8. A process, according to claim 4, wherein said ethyl succinyl chloride is added over a period of about one hour.

9. A process, according to claim 4, wherein the temperature of the reaction mixture is increased to about 35° C. before the addition of the heavy metals scavenger.

10. A process, according to claim 4, wherein the heavy metals scavenger is sodium citrate.

11. A process, according to claim 4, wherein said mixture resulting after the addition of the heavy metals scavenger is stirred for about 0.5 hour.

12. A process for preparing erythromycin ethyl succinate which comprises:
   (a) dissolving erythromycin USP quality free base in sufficient quantity in tetrahydrofuran to maintain a solution at about 35° C.;
   (b) adding a sufficient amount of a potassium carbonate solution and water to maintain the pH of the aqueous phase between about 7 and 8.5 to obtain a mixture of erythromycin USP quality free base in tetrahydrofuran and potassium carbonate solution;
   (c) cooling said mixture to about 18° C.;
   (d) adding ethyl succinyl chloride to said cooled mixture over a period of about one hour;
   (e) increasing the temperature of the reaction mixture to about 35° C. and adding sodium citrate;
   (f) stirring said mixture for about 0.5 hour;
   (g) separating the resulting lower phase from the reaction mixture;
   (h) adding a sufficient amount of diatomaceous earth to the remaining organic solution to remove any insoluble foreign particles;
   (i) filtering the remaining solution and then cooling to about 18° C. to about 20° C.; and
   (j) inducing crystallization of erythromycin ethyl succinate by adding water and seeding with erythromycin ethyl succinate crystals.

* * * * *